(12) United States Patent
Mackman

(10) Patent No.: US 6,465,503 B2
(45) Date of Patent: Oct. 15, 2002

(54) SELECTIVE UROKINASE INHIBITORS

(75) Inventor: Richard Laurence Mackman, San Bruno, CA (US)

(73) Assignee: Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/927,785

(22) Filed: Aug. 10, 2001

(65) Prior Publication Data

US 2002/0045650 A1 Apr. 18, 2002

Related U.S. Application Data

(60) Provisional application No. 60/224,712, filed on Aug. 11, 2000.

(51) Int. Cl.$^7$ .................. C07D 257/02; C07D 249/06; A61K 31/4192; A61K 31/41; A61P 43/00

(52) U.S. Cl. .............. 514/381; 514/359; 548/252; 548/255

(58) Field of Search ................. 548/252, 255; 514/381, 359

(56) References Cited

FOREIGN PATENT DOCUMENTS

| WO | WO 99 41231 A | | 8/1999 |
|---|---|---|---|
| WO | WO 00/35886 | * | 6/2000 |

* cited by examiner

*Primary Examiner*—Joseph K. McKane
*Assistant Examiner*—Andrea Small
(74) *Attorney, Agent, or Firm*—Wayne W. Montgomery; Rekha Bansal

(57) ABSTRACT

The present invention provides novel compounds of Formula I:

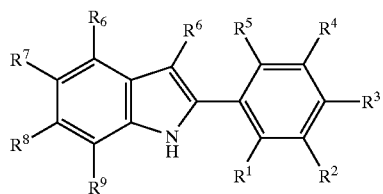

Formula I its prodrug forms, or pharmaceutically acceptable salts thereof. The compounds of this invention are inhibitors of uPA, and have utility as cancer treating agents.

10 Claims, No Drawings

SELECTIVE UROKINASE INHIBITORS

This application is based on and claims priority from U.S. Provisional Application S.No. 60/224,712 filed on Aug. 11, 2000.

FIELD OF INVENTION

The present invention relates to compounds of Formula I which are useful as Urokinase (uPA).

BACKGROUND OF THE INVENTION

One of the most active areas in cancer research is the field of proteolytic enzymes and their role in the spread of cancer. One such class of protease, that plays a significant role in the progression of cancer, are the serine proteases, in particular Urokinase-type plasminogen activator (uPA). Inhibitors of uPA have been postulated to be of therapeutic value in treating cancer.

Disclosed in U.S. Pat. No. 5,576,343 are aromatic amidine derivatives and salts thereof. These compounds comprise amidino substituted indolyl, benzofuranyl, benzothienyl, benzimidazolyl, benzoxazoyl, benzothiazolyl, naphthyl, tetrahydronaphthyl and indanyl groups, attached to a substituted phenyl ring by an alkylene group having from 1 to 4 carbon atoms.

In spite of various efforts, desirable treatment for cancer remains elusive. One of the hurdles is finding an appropriate compound which has the therapeutic attributes necessary to be an effective drug. These attributes are significantly affected by the pKa values of compounds, solubility of the compounds, bio-availability of the compound, average residence time of the compound in the blood stream, etc. There is thus a need for new compounds that will be effective in inhibiting uPA. We have surprisingly found that compounds of the present invention are selective uPA inhibitors with desirable pKa values, average residence time and enhanced bioavailability.

SUMMARY OF THE INVENTION

The present invention provides compounds of Formula I:

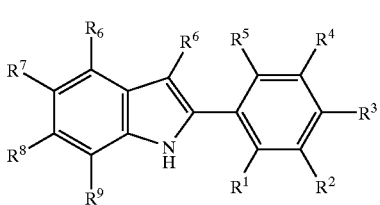

Formula I its prodrug forms or pharmaceutically acceptable salts thereof, wherein $R^1$ represents OH;
$R^2$ represents phenyl or nitrophenyl;
$R^3$ represents H;
$R^4$ represents $(CH_2)_{0-2}$-tetrazolyl or $(CH_2)_{0-2}$-triazolyl;
$R^5$ represents H;
$R^6$ represents H;
$R^7$ represents amino, amidino or guanidino;
$R^8$ represents halogen; and
$R^9$ represents H.

DETAILED DESCRIPTION

The present invention in a preferred embodiment provides a compound of Formula I selected from:

6-Chloro-2-[2-hydroxy-5-(1H-tetrazol-5-yl)-biphenyl-3-yl]-1H-indole-5-carboxamidine;
6-Fluoro-2-[2-hydroxy-5-(1H-tetrazol-5-yl)-biphenyl-3-yl]-1H-indole-5-carboxamidine;
6-Fluoro-2-[2-hydroxy-3'-nitro-5-(1H-tetrazol-5-yl)-biphenyl-3-yl]-1H-indole-5-carboxamidine;
6-Chloro-2-[2-hydroxy-3'-nitro-5-(1H-tetrazol-5-yl)-biphenyl-3-yl]-1H-indole-5-carboxamidine;
6-Chloro-2-[2-hydroxy-3'-nitro-5-(3H-[1,2,3]triazol-4-yl)-biphenyl-3-yl]-1H-indole-5-carboxamidine;
6-Chloro-2-[2-hydroxy-5-(3H-[1,2,3]triazol-4-yl)-biphenyl-3-yl]-1H-indole-5-carboxamidine;
6-Fluoro-2-[2-hydroxy-5-(3H-[1,2,3]triazol-4-yl)-biphenyl-3-yl]-1H-indole-5-carboxamidine; and
6-Fluoro-2-[2-hydroxy-3'-nitro-5-(3H-[1,2,3]triazol-4-yl)-biphenyl-3-yl]-1H-indole-5-carboxamidine.

Another preferred embodiment provides a compound of Formula I

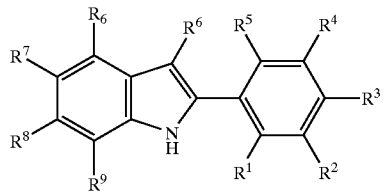

Formula I its prodrug forms or pharmaceutically acceptable salts of, wherein $R^1$ represents OH;
$R^2$ represents phenyl;
$R^3$ represents H;
$R^4$ represents tetrazolyl or triazolyl;
$R^5$ represents H;
$R^6$ represents H;
$R^7$ represents amino, guanidino or amidino;
$R^8$ represents halogen; and
$R^9$ represents H.

Provided in yet another preferred embodiment is a compound of Formula I:
wherein $R^1$ represents OH;
$R^2$ represents nitrophenyl;
$R^3$ represents H;
$R^4$ represents tetrazolyl or triazolyl;
$R^5$ represents H;
$R^6$ represents H;
$R^7$ represents amidino;
$R^8$ represents halogen; and
$R^9$ represents H.

Another aspect of the present invention provides a pharmaceutical composition comprising a pharmaceutically acceptable carrier and a therapeutically effective amount of a compound according of Formula I, or a pharmaceutically acceptable salt thereof.

Yet another aspect of the present invention provides a method for treating or preventing a cancer related disorder, comprising administering to a patient/mammal in need thereof, a therapeutically effective amount of a compound of Formula I or a pharmaceutically acceptable salt thereof.

Synthesis

The novel compounds of the present invention can be prepared in a number of ways known to one skilled in the art of organic synthesis. Described herein are some of the synthetic methods for synthesizing novel compounds of the present invention. All temperatures reported herein are in degrees Celsius (° C.), unless indicated otherwise.

The novel compounds of Formula I can be prepared using the reactions and synthetic techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group, if necessary, used for the protection of the reactive functional groups present in the compounds described in this invention. An authoritative account describing the many alternatives to the trained practitioner is Greene and Wuts (Protective Groups in Organic Synthesis, Wiley and Sons, 1991). Proton NMR's ($^1$H NMR) were obtained using deuterated solvents such as dimethyl sulfoxide (DMSO-d$_6$), deuterated chloroform (CDCl$_3$), or other appropriate solvents.

EXPERIMENTAL

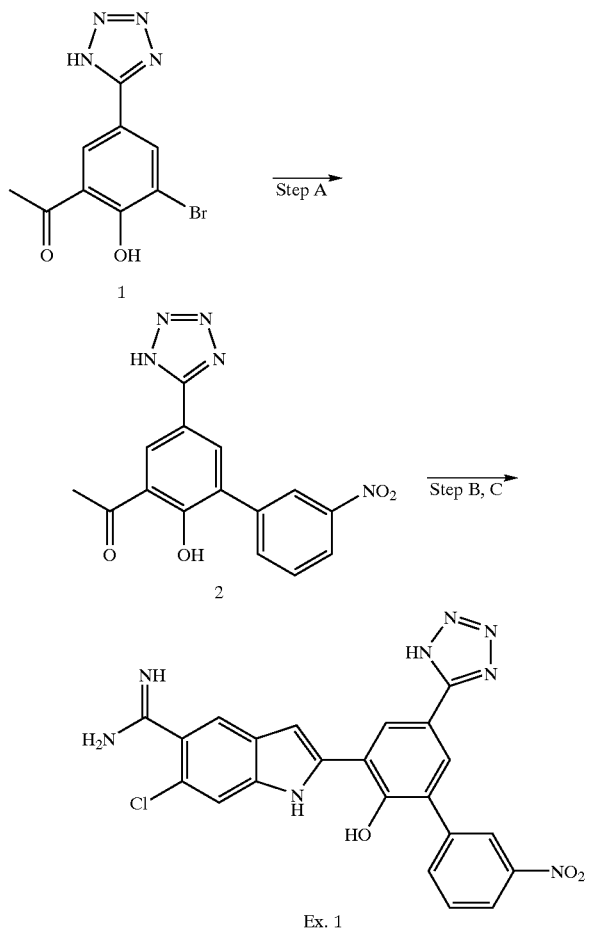

Preparation of 6-Chloro-2-[2-hydroxy-3'-nitro-5-(1H-tetrazol-5-yl)-biphenyl-3-yl]-1H-indole-5-carboxamidine, Ex. 1

Step-A: 1-[2-Hydroxy-3-nitro-5-(1H-tetrazol-5-yl)-biphenyl-3-yl]-ethanone 2

A solution of 1-[3-bromo-2-hydroxy-5-(1H-tetrazol-5-yl)-phenyl]-ethanone (1, 1.07 g, 3.78 mmoles) and 3-nitrophenylboronic acid (0.69 g, 5.67 mmoles) in ethanol (8 mL) was mixes with toluene (25 mL), 2M Na2CO3 (2.8 mL) and the resulting mixture flushed with nitrogen. The nitrogen flushed reaction mixture then was combined with Pd(PPh$_3$)$_4$ (0.44 g, 0.38 mmoles) and the resulting solution was refluxed from about 8 to about 16 hours. The reaction mixture then was cooled to ambient temperature, acidified with 1N HCl and extracted with EtOAc (2×150 mL). The combined organic extracts were washed with brine, dried over anhydrous sodium sulfate and concentrated to afford compound 2 product as a colorless oil (1.22, 100%). MS (ESI, M$^+$+1): Calc. 325.08; Found 325.9.

Steps-B,C: 6-Chloro-2-[2-hydroxy-3'-nitro-5-(1H-tetrazol-5-yl)-biphenyl-3-yl]-1H-indole-5-carboxamidine Ex. 1

A solution of 1-[2-Hydroxy-5-(1H-tetrazol-5-yl)-biphenyl-3-yl]-ethanone (2, 1.20 g, 3.69 moles), 3-chloro-4-hydrazinobenzamidine (1.74 g, 7.80 mmoles) and DIEA (2.72 mL, 15.6 mmoles) in EtOH (50 mL) was refluxed from about 8 to about 16 hours. As the reaction proceeded, the yellow colored hydrazone precipitated out of solution. The reaction mixture was cooled and concentrated under reduced pressure to yield a yellowish powder. The yellowish powder was washed with acetonitrile and dried to yield about 1.50 g. The dry hydrazone was mixed with polyphosphoric acid (5 mL) and the resulting mixture was agitated at a temperature of about 165° C. for about an hour. The agitated mixture then was cooled and mixed with ice to form a brownish precipitate which was purified by reverse phase HPLC and lyophilized to afford the product as a cream colored solid (50 mgs, 3%). MS (ESI, M$^+$+1): Calc. 440.13; Found 440.6.

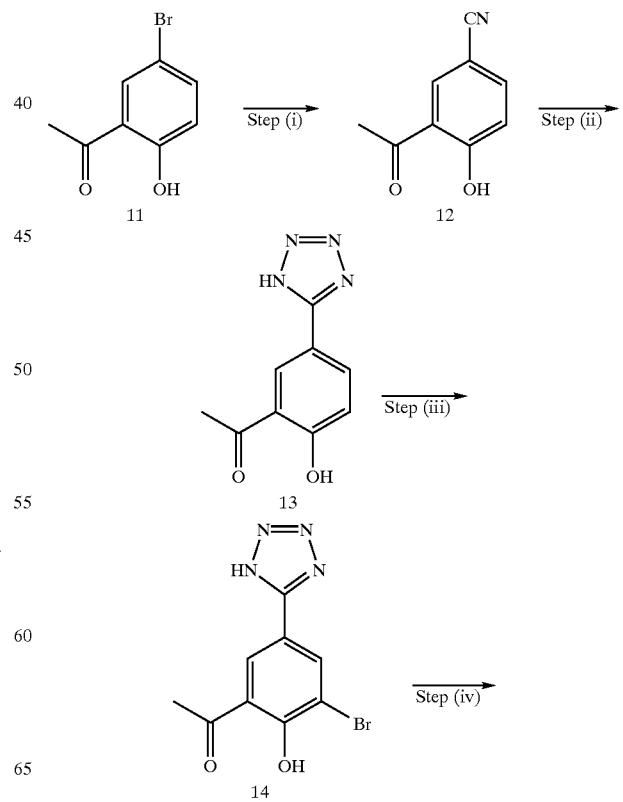

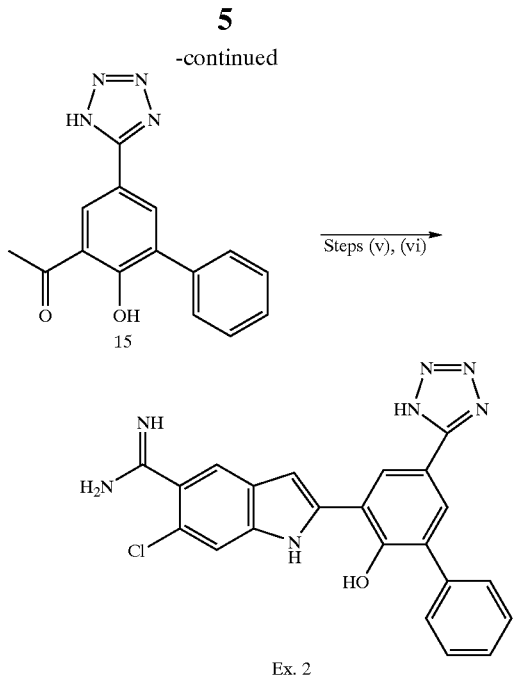

Ex. 2

Preparation of 6-Chloro-2-[2-hydroxy-5-(1H-tetrazol-5-yl)-biphenyl-3-yl]-1H-indole-5-carboxamidine Ex. 2

Step-(i): 3-Acetyl-4-hydroxy-benzonitrile 12

A solution of 5-bromo-2-hydroxyacetophenone (11, 10.00 g, 46.5 mmoles) in anhydrous DMF (25 mL) was mixed with copper cyanide (6.25 g, 69.75 mmoles) and the resulting reaction mixture was heated for about 8 to 16 hours at a temperature of about 160° C. The reaction mixture was cooled to room temperature and mixed with ether, the ether mixture was filtered through celite and the filtrate concentrated to afford a solid which was purified by flash column chromatography through silica using Hexane/EtOAc (4:1) as eluant to yield compound 12 as a clear colorless oil (5.25 g, 70%).

$^1$H-NMR (DMSO-$\delta$6) d: 8.31 (s, 1H), 7.92 (d, 1H, J=8.4 Hz), 7.12 (d, 1H, J=8.7 Hz), 2.65 (s, 3H).

Step-(ii): 1-[2-Hydroxy-5-(1H-tetrazol-5-yl)-phenyl]-ethanone 13

A solution of 3-acetyl-4-hydroxybenzonitrile 12 (2.23 g, 13.97 mmoles) in toluene was mixed with azidotributyltin (5.74 mL, 20.96 mmoles) and the resulting mixture was refluxed for about 8 to 18 hours. The reaction mixture was cooled to ambient temperature under a stream of nitrogen and then was mixed with 6N HCl (10 mL). The resulting mixture was agitated at room temperature for about 30 minutes, and then was concentrated under reduced pressure to yield a tan colored solid. Trituration of the solid with hexane afforded compound 13 as a pale tan colored solid (2.80 g, 99%). MS (ESI, M$^+$+1): Calc. 204.06; Found 205.0.

Step-(iii): 1-[3-Bromo-2-hydroxy-5-(1H-tetrazol-5-yl)-phenyl]-ethanone 14

A solution of 1-[2-hydroxy-5-(1H-tetrazol-5-yl)-phenyl]-ethanone (13, 1.00 g, 4.9 mmoles) in anhydrous DMF (10 mL) was mixed with N-bromosuccinimide (1.31 g, 7.45 mmoles) and the resulting reaction mixture was agitated at 65° C. for two hours. The reaction mixture then was diluted with EtOAc, washed with water and extracted with EtOAc (2×100 mL). The combined organic extracts were washed with brine, dried over anhydrous sodium sulfate and concentrated to afford the title compound of formula 14 as a pale yellow oil (1.24 g, 89%). MS (ESI, M$^+$+1): Calc. 281.98; Found 283.0.

Step-(iv): 1-[2-Hydroxy-5-(1H-tetrazol-5-yl)-biphenyl-3-yl]-ethanone 15

A solution of 1-[3-bromo-2-hydroxy-5-(1H-tetrazol-5-yl)-phenyl]-ethanone (14, 1.24 g, 4.38 mmoles) and benzene boronic acid (0.80 g, 6.57 mmoles) in ethanol (8 mL) was mixed with toluene (25 mL), 2M Na$_2$CO$_3$ (3.3 mL) and the resulting mixture flushed with nitrogen. Pd(PPh$_3$)$_4$ (0.51 g, 0.44 mmoles) was added and the resulting reaction mixture was refluxed for up to 18 hours. The reaction mixture then was acidified with 1N HCl and extracted with EtOAc (2×150 mL). The combined organic extracts were washed with brine, dried over anhydrous sodium sulfate and concentrated to afford the title compound of formula 15 as a colorless oil (1.15, 93%). MS (ESI, M$^+$+1): Calc. 280.102; Found 281.0.

Steps-(v),(vi): 6-Chloro-2-[2-Hydroxy-5-(1H-tetrazol-5-yl)-biphenyl-3-yl]-1H-indole-5-carboxamidine Ex. 2

A solution of 1-[2-Hydroxy-5-(1H-tetrazol-5-yl)-biphenyl-3-yl]-ethanone 15 (0.500 g, 1.77 moles), 3-chloro, 4-hydrazinobenzamidine (0.79 g, 3.53 mmoles) and DIEA (1.23 mL, 7.06 mmoles) in EtOH (25 mL) is refluxed for up to 18 hours. As the reaction proceeds, a yellow colored hydrazone precipitates out of the solution. The reaction mixture is cooled and the solvents removed under reduced pressure to yield a yellow powder. The yellow powder is washed with acetonitrile and isolated by vacuum filtration (0.45 g, %). The yellow powder (hydrazone) is mixed with polyphosphoric acid (1 mL) and the resulting mixture is agitated at a temperature of about 165° C. for about an hour. The agitated mixture then is cooled and mixed with ice to form a brownish precipitate which is purified by reverse phase HPLC and lyophilized to afford the title compound, Ex. 2.

Utility

Compounds of the present invention are useful as inhibitors of Urokinase (uPA) which has been postulated to have therapeutic value in treating cancer.

Compounds of the present invention show selectivity for inhibiting uPA. The effectiveness of compounds of the present invention as inhibitors of Urokinase is determined using synthetic substrates and purified Urokinase.

The rates of hydrolysis by the chromogenic substrates are measured both in the absence and presence of compounds of the present invention. Hydrolysis of the substrates result in the release of the -pNA moiety, which is monitored spectrophotometrically by measuring the increase in absorbance at 405 nanometer (nm). A decrease in the rate of absorbance change at 405 nm in the presence of a inhibitor is indicative of enzyme inhibition. The results of this assay are expressed as the inhibitory constant, Ki app.

Urokinase inhibition determinations are made in 50 mM Tris (pH7.5), 150 mM NaCl, 0.05% Tween-20, 0.002% antifoam, and 1 mM EDTA with Human Urokinase (from American Diagnostica, CT,USA). Values of Ki app. were determined by allowing 20 nM human Urokinase to react with the Pefachrome substrate (0.3 mM, Centerchem, Conn., USA) in the presence of an inhibitor. Hydrolysis of the chromogenic substrate is followed spectrophotometrically at 405 nm for five minutes. The enzyme assay routinely yielded linear progression curves under these conditions. Initial velocity measurements calculated from the progress curves by a kinetic analysis program (Batch Ki; Peter Kuzmic, BioKin, Ltd., Madison, Wis.) are used to determine Ki app.

DEFINITIONS

As used herein, the following terms and abbreviations have the following meaning, unless indicated otherwise.

The term "prodrug" is intended to represent covalently bonded carriers which are capable of releasing the active ingredient of Formula I, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula I include compounds wherein a hydroxy, amidino, guanidino, amino, carboxylic or a similar group is modified. The term "halogen" represents Cl, F, Br and I.

"Pharmaceutically acceptable salts" is as understood by one skilled in the art. Thus a pharmaceutically acceptable salt includes acid or base salts of compounds of Formula I. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in, for example, *Remington's Pharmaceutical Sciences,* 17th ed., Mack Publishing Company, Easton, Pa., 1985, which is incorporated herein by reference.

What is claimed is:

1. A compound of Formula I

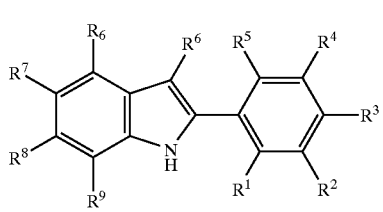

Formula I its prodrug forms or pharmaceutically acceptable salts thereof, wherein $R^1$ represents OH;

$R^2$ represents phenyl or nitrophenyl;

$R^3$ represents H;

$R^4$ represents $(CH_2)_{0-2}$-tetrazolyl or $(CH_2)_{0-2}$-triazolyl;

$R^5$ represents H;

$R^6$ represents H;

$R^7$ represents amino, amidino or guanidino;

$R^8$ represents halogen; and $R^9$ represents H.

2. A compound of claim 1 selected from
6-Chloro-2-[2-hydroxy-5-(1H-tetrazol-5-yl)-biphenyl-3-yl]-1H-indole-5-carboxamidine;
6-Fluoro-2-[2-hydroxy-5-(1H-tetrazol-5-yl)-biphenyl-3-yl]-1H-indole-5-carboxamidine;
6-Fluoro-2-[2-hydroxy-3'-nitro-5-(1H-tetrazol-5-yl)-biphenyl-3-yl]-1H-indole-5-carboxamidine;
6-Chloro-2-[2-hydroxy-3'-nitro-5-(1H-tetrazol-5-yl)-biphenyl-3-yl]-1H-indole-5-carboxamidine;
6-Chloro-2-[2-hydroxy-3'-nitro-5-(3H-[1,2,3]triazol-4-yl)-biphenyl-3-yl]-1H-indole-5-carboxamidine;
6-Chloro-2-[2-hydroxy-5-(3H-[1,2,3]triazol-4-yl)-biphenyl-3-yl]-1H-indole-5-carboxamidine;
6-Fluoro-2-[2-hydroxy-5-(3H-[1,2,3]triazol-4-yl)-biphenyl-3-yl]-1H-indole-5-carboxamidine; and
6-Fluoro-2-[2-hydroxy-3'-nitro-5-(3H-[1,2,3]triazol-4-yl)-biphenyl-3-yl]-1H-indole-5-carboxamidine.

3. A compound of Formula I

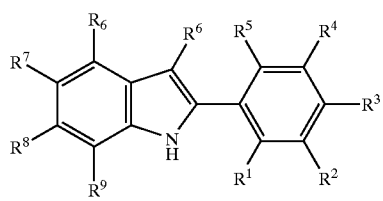

Formula I its prodrug form or pharmaceutically acceptable salt thereof, wherein $R^1$ represents OH;

$R^2$ represents phenyl;

$R^3$ represents H;

$R^4$ represents tetrazolyl or triazolyl;

$R^5$ represents H;

$R^6$ represents H;

$R^7$ represents amidino;

$R^8$ represents halogen; and $R^9$ represents H.

4. A compound of Formula I:

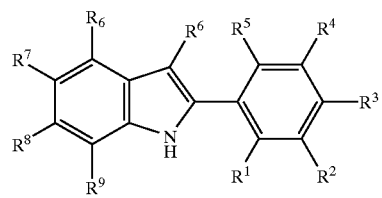

wherein $R^1$ represents OH;

$R^2$ represents nitrophenyl;

$R^3$ represents H;

$R^4$ represents tetrazolyl or triazolyl;

$R^5$ represents H;

$R^6$ represents H;

$R^7$ represents amidino;

$R^8$ represents halogen; and $R^9$ represents H.

5. A pharmaceutical composition comprising a pharmaceutically acceptable carrier and a therapeutically effective amount of a compound of claim 1, or a pharmaceutically acceptable salt thereof.

6. A method for treating a cancer related disorder, comprising administering to a patient/mammal in need thereof a therapeutically effective amount of a compound of claim 1 or a pharmaceutically acceptable salt thereof.

7. A pharmaceutical composition comprising a pharmaceutically acceptable carrier and a therapeutically effective amount of a compound of claim 3, or a pharmaceutically acceptable salt thereof.

8. A method for treating a cancer related disorder, comprising administering to a patient/mammal in need thereof a therapeutically effective amount of a compound of claim 3 or a pharmaceutically acceptable salt thereof.

9. A pharmaceutical composition comprising a pharmaceutically acceptable carrier and a therapeutically effective amount of a compound of claim 4, or a pharmaceutically acceptable salt thereof.

10. A method for treating a cancer related disorder, comprising administering to a patient/mammal in need thereof a therapeutically effective amount of a compound of claim 4 or a pharmaceutically acceptable salt thereof.

* * * * *